US008663985B2

(12) United States Patent
Miltenyi et al.

(10) Patent No.: US 8,663,985 B2
(45) Date of Patent: Mar. 4, 2014

(54) ANCHORING/CAPTURING SYSTEM FOR SELECTING OR ANALYZING A CHO CELL ACCORDING TO A PRODUCT SECRETED BY THE CHO CELL

(75) Inventors: Stefan Miltenyi, Bergisch Gladbach (DE); Susanne Hoher-Peters, Bergisch Gladbach (DE); Monika Winkels, Lindlar (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 230 days.

(21) Appl. No.: 13/098,498

(22) Filed: May 2, 2011

(65) Prior Publication Data
US 2011/0269152 A1 Nov. 3, 2011

(30) Foreign Application Priority Data
May 2, 2010 (EP) .................................. 10004611

(51) Int. Cl.
*C12N 5/07* (2010.01)
*G01N 33/53* (2006.01)
*G01N 33/574* (2006.01)

(52) U.S. Cl.
USPC ............... 435/358; 435/2; 435/7.1; 435/7.23; 435/326; 435/362; 435/374; 435/383; 436/512; 436/513; 436/517; 436/538; 436/540; 436/548; 436/63; 436/64

(58) Field of Classification Search
USPC ........ 435/7.1, 7.2, 7.5, 326, 328, 358, 362, 2, 435/7.23, 374, 383; 436/513, 517, 518, 436/526, 548, 546, 63, 512, 538, 540
See application file for complete search history.

(56) References Cited

U.S. PATENT DOCUMENTS

| 6,576,428 | B1 | 6/2003 | Assenmacher |
| 7,166,423 | B1 | 1/2007 | Miltenyi |
| 7,435,553 | B2 | 10/2008 | Fandl |
| 2004/0219611 | A1 | 11/2004 | Racher |
| 2005/0186623 | A1 | 8/2005 | Fandl |
| 2005/0221325 | A1 | 10/2005 | Thill |
| 2009/0137416 | A1 | 5/2009 | Fandl |

FOREIGN PATENT DOCUMENTS

WO            WO0042176            7/2000

OTHER PUBLICATIONS

Manz et al. Analysis and sorting of live cells according to secreted molecules, relocated to a cell-surface affinity matrix, Proc. Natl. Acad. Sci. USA, 92:1921-1925 (Mar. 1995)).*
Caron et al. Fluorescent labeling in semi-solid medium for selection of mammalian cells secreting high-levels of recombinant protein, Biotechnology 6 (42): 1-33 (May 11, 2009)).*
Hoch, Ash, Dissertation, May 20, 2010, and English language translation of Abstract, Abstract only.
Manz et al., Analysis and . . . affinity matrix, PNAS 92, 1921-1925, 1995.

(Continued)

*Primary Examiner* — Gail R Gabel
(74) *Attorney, Agent, or Firm* — MDIP LLC (57) ABSTRACT

An anchoring/capturing system for selecting or analyzing a CHO cell according to a product secreted by the CHO cell is described. The anchoring/capturing system comprises a first antibody or a first antigen-binding fragment for anchoring to the extracellular surface of the CHO cell, and a second antibody or a second antigen-binding fragment for binding the secreted product. Uses and methods involving the anchoring/capturing system are provided.

9 Claims, 5 Drawing Sheets

(56) References Cited

OTHER PUBLICATIONS

Manz et al., "Flow cytometric . . . cells," Cytometry Suppl 9, 43-44, 1998.

Brosterhus et al., "Enhancement and . . . cytokine secretion . . . " Eur J Imm 29, 4053-4059, 1999.

Akselband et al., "Isolation of . . . secretion assay," Assay Drug Devel Tech 1, 619-626, 2003.

Brezinsky et al., "A simple . . . productivity," J Imm Methods 277, 141-155, 2003.

Caron et al. "Fluorescent..proteins," BMC Biotech 9, 42, 2009.

Holmes et al., "Improved cell . . . high secretors," J Imm Methods 230, 141-147, 1999.

Hanania et al., "Automated . . . producers," Biotech Bioeng 91, 872-876, 2005.

Dzionek et al., "BDCA-2 . . . peripheral blood," Imm 165, 6037-6046, 2000.

* cited by examiner

ANCHORING/CAPTURING SYSTEM FOR SELECTING OR ANALYZING A CHO CELL ACCORDING TO A PRODUCT SECRETED BY THE CHO CELL

The instant application claims benefit to EPO Ser. No. 10004611.9 filed 2 May 2010, the contents of which are herein incorporated by reference in entirety.

FIELD OF THE INVENTION

The invention pertains to an anchoring/capturing system for selecting or analyzing a CHO cell according to a product secreted by the CHO cell, as well as to uses thereof.

The invention is in the field of analysis of cell populations and cell separation and the compositions obtained thereby. More particularly, the invention pertains to an anchoring/capturing system for selecting or analyzing a CHO cell according to a product secreted by the CHO cell, as well as to uses thereof.

BACKGROUND OF THE INVENTION

Numerous attempts have been made to analyze populations of cells and to separate cells based on the products that they produce. Such approaches to cell analysis and separation are especially useful in assessing those cells which are capable of secreting a desired product (the "product") or which are relatively high secretors of the product. These methods include cloning in microtiter plates and analysis of the culture supernatant for product; and cloning in agar and analysis by methods for identification of the product of the localized cells; the identification methods including, for example, plaque assays and western blotting. Most methods for analysis and selection of cells based on product secretion involve physically isolating the cell, followed by incubation under conditions that allow product secretion, and screening of the cell locations to detect the cell or cell clones that produce the product. When cells are in suspension, after the cells have secreted the product, the product diffuses from the cell without leaving a marker to allow identification of the cell from which it was secreted. Thus, secretor cells cannot be separated from non-secretor cells with these types of systems.

The affinity matrix technology was established by Manz and coworkers (1995) to study the secretion of antibodies by hybridomas and cytokine secretion of activated T lymphocytes. To create an artificial affinity matrix on the cell surface, primary amine residues of surface molecules were biotinylated. Next, cells were labeled directly with an avidinated catch antibody specific for the secreted molecule. Afterwards, cells were allowed to secrete in gelatin, a medium with decreased permeability to reduce diffusion of the secreted molecule. The catch antibody could then capture the secreted molecules in the vicinity of the cell surface. Secreting cells were subsequently labelled with fluorescent reagents, specific for the secreted molecule, to allow flow cytometric analysis and cell sorting. Borth et al. (Biotechnology and Bioengeneering, 2001, 71: 266-273) used this technique to select for high producing subclones of antibody-secreting CHO cells. CHO cells provide glycosylation patterns of the synthesized proteins that are similar to those provided in human cells. Such proteins are particularly suitable as therapeutic proteins.

A further development of this technique was the use of an (neutr)avidin bridge and a biotinylated antibody instead of an avidinated antibody to maximize the binding capacity of the matrix. Furthermore, the CHO cells were embedded in medium with only 10% gelatin. Holmes and Al-Rubeai (1999) named this method the affinity capture surface display (ACSD).

An alteration of the ACSD method was introduced by Carroll and Al-Rubeai (2005) that replaced fluorescent activated cell sorting by magnetic activated cell sorting to improve cell viability of fragile cells.

In these approaches, the extracellular surface of the CHO cells is chemically treated to allow for a capturing moiety to bind to the extracellular surface of the CHO cells. Moreover, these approaches are laborious and thus disadvantageous.

SUMMARY OF THE INVENTION

It was an object of the present invention to provide an alternative approach for selecting or analyzing a CHO cell according to a product secreted by the CHO cell.

In an aspect, an anchoring/capturing system for selecting or analyzing a CHO cell according to a product secreted by the CHO cell, comprising a first antibody or a first antigen-binding fragment for anchoring to the extracellular surface of the CHO cell, and a second antibody or a second antigen-binding fragment for binding the secreted product is provided.

In another embodiment a method for selecting or analyzing a CHO cell according to a product secreted by the CHO cell, comprising binding an anchoring/capturing system to the surface of the CHO cell for capturing the product, wherein the anchoring/capturing system comprises a first antibody or a first antigen-binding fragment for anchoring to the extracellular surface of the CHO cell, and a second antibody or a second antigen-binding fragment for binding the secreted product; culturing the cell under conditions wherein the product is secreted and specifically bound to the second antibody or to the second antigen-binding fragment; labeling the product with a detectable label; and selecting or analyzing the cell on the basis of the bound and labeled product is provided.

In another embodiments, use of the method of interest to select and to analyse a CHO cell is provided, cells, antibodies and kits are disclosed for use in or as obtained in the practice of methods of interest are described.

The present invention provides methods for detecting, analyzing and separating secreting CHO cells on the basis of secreted product. The methods are based on capture and relocation to the cell surface of the secreted product. The captured product permits the cell to be detected, analyzed and, if desired, sorted, according to the presence, absence or amount of the product present. The system of capture comprises a product-specific anchoring/capturing system.

BRIEF DESCRIPTION OF THE FIGURES

The following description of the figures and the respective drawings are non-limiting examples that depict various embodiments that exemplify the present invention.

FIG. 3. Schematic picture of a preferred embodiment of the present invention (Human Antibody CHO Capture System). For labeling of the CHO cells, an anchoring/capturing system (also "a catch reagent") consisting of the αCHO antibody as the first antibody of the anchoring/capturing system and αhuman IgG antibody as the second antibody of the anchoring/capturing system was used. The cells were allowed to secrete humanized CD303 during a secretion period of 1 hr in warm CD CHO medium (37° C.). The secreted antibody was immobilized by the catch reagent near the cell surface and was detected with an αhuman Igκ-biotin antibody. To fluorescently stain the cells, conjugates of an αbiotin antibody coupled to R-phycoerythrin (PE) were used. Cells were magnetically labeled with an αPE-MicroBead conjugate. Separation was performed with 2 MS columns.

FIG. 4. Secretion assay and magnetic cell sorting. Secretion assay was carried out on CHO pool 3/L cells. Shown are a negative control (A) and a positive control with staining of Tysabri-PE (B) as small-scale detection approaches without separation. The two fractions of the large-scale approach were the original fraction before separation (C) and the positive fraction of the second MS column (D). Dot plots A, C and D show staining with anti-human Igκ on the x-axis (against the sideward scatter on the y-axis). All samples were measured at MACSQuant® Analyzer and dead cells were excluded by a PI gate.

DETAILED DESCRIPTION OF THE INVENTION

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual," second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987, and periodic updates); "PCR: The Polymerase Chain Reaction", (Mullis et al., eds., 1994); and "Current Protocols in Immunology" (J. E. Coligan et al., eds., 1991).

Cell sorting and cell analysis methods are known in the art and are described in, for example, The Handbook of Experimental Immunology, Volumes 1 to 4, (D. N. Weir, editor) and Flow Cytometry and Cell Sorting (A. Radbruch, editor, Springer Verlag, 1992).

The term "selecting" may comprise also enriching and isolating. The term, "substantially enriched," as used herein, indicates that a cell population is at least about 50-fold, more preferably at least about 500-fold, and even more preferably at least about 5000-fold or more enriched from an original mixed cell population comprising the desired cell population.

The present invention provides methods for obtaining a cell population enriched in CHO cells which secrete a product.

As the anchoring/capturing system may comprise a first antigen-binding fragment for anchoring to the extracellular surface of the CHO cell, and a second antigen-binding fragment for binding the secreted product, the anchoring/capturing system can be, in one embodiment of the invention, a bispecific antibody.

"Bispecific antibody" and "bispecific antibodies," also known as bifunctional antibodies, intends antibodies that recognize two different antigens by virtue of possessing at least one first antigen combining site specific for a first antigen or hapten, and at least one second antigen combining site specific for a second antigen or hapten. Such antibodies can be produced by recombinant DNA methods or include, but are not limited to, antibodies made chemically by methods known in the art.

Chemically created bispecific antibodies have been reduced and reformed so as to retain their bivalent characteristics. Antibodies that have been chemically coupled can have at least two antigen recognition sites for each antigen.

In a preferred embodiment, this anchoring/capturing system is a conjugate of at least two antibodies or antigen-binding fragments that were chemically joined, preferably at the Fc moiety. Methods for conjugating are known to a person of skill in the art.

Preferably, the first antibody or the first antigen-binding fragment of the anchoring/capturing system binds specifically to a surface molecule of the CHO cell, thereby anchoring the anchoring/capturing system to the CHO cell. For the second antibody or a second antigen-binding fragment to be able to bind the product from the CHO cell, the first antibody or antigen-binding fragment must be oriented such that the second antibody or antigen-binding fragment that binds the product is not sterically hindered.

It is further preferred that the first antibody or the first antigen-binding fragment for anchoring the anchoring/capturing system to the extracellular surface of the CHO cell is a monoclonal antibody or an antigen-binding fragment thereof, in particular the monoclonal antibody HA3-21F5.6 or an antigen-binding fragment thereof.

In an embodiment, an anchoring/capturing system is one wherein the first antibody is the monoclonal antibody HA3-21F5.6 that is being secreted by the hybridoma cell line that was deposited at the German Collection of Microorganisms and Cell Cultures (DSMZ), Braunschweig, Germany, on Apr. 30, 2010 and granted accession number DSM ACC3063. The generation of this first antibody is described in the examples.

The first antibody can recognize a target on the extracellular surface of the CHO cell that is constitutively expressed. In another embodiment, the first antibody recognizes a target on the extracellular surface of the CHO cell that is expressed on induction of the cell with a chemical inducer.

The second antibody or the second antigen-binding fragment of the anchoring/capturing system can be one, for example, specifically binding a CD303 (BDCA-2) antibody as the product. CD303 (BDCA-2) is a $Ca^{2+}$-dependent type II C-type lectin that is specifically expressed by human plasmacytoid dendritic cells (Rock et al., 2007).

In contrast to other systems in the art for selecting or analyzing a CHO cell according to a product secreted by the CHO cell, the present invention does not depend on a chemical modification of molecules on the surface of the CHO cell. Moreover, no streptavidin, avidin or like need be used for direct treatment of the CHO cell.

In a preferred embodiment of the method, the cells that have a secreted product bound to the second antibody or the second antigen-binding fragment of the anchoring/capturing system are not lysed as part of the selection or analysis but remain intact.

The product that is being secreted from the CHO cell preferably is a protein, in particular an antibody or an antigen-binding fragment of an antibody. The antigen-binding fragment can be chosen from the group consisting of whole antibodies, bispecific antibodies, chimeric antibodies, $F_{ab}$, $F_{(ab')2}$, single chain V region fragments ($scF_v$), fusion proteins, aptamers, carbohydrates and lectins.

An exemplified secreted antibody is an antibody against the molecule CD303 (BDCA-2), which is known in the art.

If the secreted product is an antibody, then it is preferably chosen from the group consisting of humanized antibodies, chimeric antibodies, human antibodies, and antigen-binding fragments thereof.

After binding of the product to the CHO cell via the anchoring/capturing system, the cell may be detectably labeled, e.g. using a third or fourth antibody, each antibody carrying a detectable label (the same or different labels). By using different antibodies, a stronger signal for detection may be generated.

The detectable label may comprise at least one of the group consisting of magnetic particles, fluorophores, radioactive isotopes, haptens and chromophores. The labeled cells can then be separated using standard cell sorting techniques based on these labels. Such techniques include, but are not limited to, flow cytometry, FACS, high gradient magnetic separation centrifugation. When the label is a magnetic particle, magnetic cell sorting (MACS) can be used to identify CHO cells excreting the product or excreting the product at certain levels. Thereby, CHO cell lines with certain secretion characteristics can be obtained, such as highly excreting CHO cell lines.

Preferred magnetic labeling methods include colloidal superparamagnetic particles in a size range of 5 to 200 nm, preferably in a size of 10 to 100 nm. The magnetic particles allow a quantitative magnetic labeling of cells, thus the amount of coupled magnetic label is proportional to the amount of bound product, and the magnetic separation methods are sensitive to different amounts of product secretion.

Colloidal particles with various specificities are known in the art, and are available, for example, through Miltenyi Biotec GmbH. The use of immunospecific fluorescent or magnetic liposomes can also be used for quantitative labeling of captured product.

In these cases, the liposomes contain magnetic material and/or fluorescent dyes conjugated with antibody on their surfaces, and magnetic separation is used to allow optimal separation between nonproducing, low producing, and high producing cells.

The magnetic separation can be accomplished with high efficiency by combining a second force to the attractive magnetic force, causing a separation based on the different strengths of the two opposed forces. Typical opposed forces are, for example, forces induced by magnetic fluids mixed in the separation medium in the magnetic separation chamber, gravity and viscous forces induced by flow speed of medium relative to the cell. Any magnetic separation method, preferably magnetic separation methods allowing quantitative separation can be used. It is also contemplated that different separation methods can be combined, for example, magnetic cell sorting can be combined with FACS, to increase the separation quality or to allow sorting by multiple parameters.

Preferred techniques include high gradient magnetic separation (HGMS), a procedure for selectively retaining magnetic materials in a chamber or column disposed in a magnetic field. In one application of this technique, the product is labeled by attaching it to a magnetic particle. The attachment is generally through association of the product with a label moiety which is conjugated to a coating on the magnetic particle which provides a functional group for the conjugation. The captured product thus coupled to a magnetic "label", is suspended in a fluid, which is then applied to the chamber. In the presence of a magnetic gradient supplied across the chamber, the magnetically labeled target cell is retained in the chamber; if the chamber contains a matrix, it becomes associated with the matrix. Cells which do not have or have only a low amount of magnetic labels pass through the chamber.

The retained cells can then be eluted by changing the strength of, or by eliminating, the magnetic field or by introducing a magnetic fluid. The selectivity for a captured product is supplied by the label moiety conjugated either directly or indirectly to the magnetic particle or by using a primary antibody and a magnetic particle recognizing the primary antibody. The chamber across which the magnetic field is applied is often provided with a matrix of a material of suitable magnetic susceptibility to induce a high magnetic field gradient locally in the camber in volumes close to the surface of the matrix. This permits the retention of fairly weakly magnetized particles. Publications describing a variety of HGMS systems are known in the art, and include, for example, U.S. Pat. Nos. 4,452,773, 4,230,685, PCT application WO85/04330, U.S. Pat. No. 4,770,183, and PCT/EP89/01602; systems are also described in U.S. Pat. Nos. 5,411,863; 5,543,289; 5,385,707; and 5,693,539, which are commonly owned and hereby incorporated herein by reference.

These conditions are known to those of skill in the art and include, inter alia, appropriate temperature, pH and concentrations of salts, growth factors and substrates in the incubation medium, as well as the appropriate concentrations of gas in the gaseous phase. When it is desirable to distinguish between high and low producer cells, the time of incubation is such that product secretion by the cells is still in a linear phase. The appropriate conditions can be determined empirically and such a determination is within the skill of one in the art.

Additionally, cell secretion can be modified, that is, upregulated, induced or reduced using a biological modifier. The biological modifiers can be added at any time but are preferably added to the incubation medium. Alternatively, the cells can be pretreated with these agents or cells prior to the incubation step. Suitable biological modifiers include, but are not limited to, molecules and other cells.

Suitable molecules include, but are not limited to, drugs, cytokines, small molecules, hormones, combinations of interleukins, lectins and other stimulating agents, e.g., PMA, LPS, bispecific antibodies and other agents that modify cellular functions or protein expression.

The culturing conditions are also such that product is essentially not captured or is captured to a much lesser extent by another cell, so as to distinguish non-producing cells from product producing cells, or high producers from low producers. Generally, the incubation time is between five minutes and ten hours, and is more usually between one and five hours. The incubation medium can optionally include a substance that slows diffusion of the product from the producer cell.

In a preferred embodiment, the CHO cell is cultured in a medium that is not viscous, in contrast to methods used in the state of the art.

It is possible that the CHO cell secretes more than one product. In that case, more than one anchoring/capturing system may be used in the invention as is understood by a person of skill in the art.

The invention now will be exemplified in the following non-limiting examples.

EXAMPLES

Preparation of CHO Cells

As CHO cells in suspension retained some of their adherent growth characteristics and tended to clump in suspension, treatment of cells was necessary to receive a single-cell suspension. Therefore, cells of a defined volume were pelleted by centrifugation (10'/100 g/20° C.). Afterwards, the pellet was resuspended in 10% of Trypsin/EDTA (Sigma) for approximately 5 min at room temperature (abbreviated RT). Progress of singularisation was continuously observed by light microscopy. When singularisation was complete, CD CHO medium (Gibco) was added up to the previous volume. After pelleting (10'/100 g/20° C.), cells were resuspended in fresh CD CHO medium. In all experiments, cells were pre-diluted to densities allowing linear growth to maintain high cell viability one day before experiment.

Generation of αCHO Antibodies (First Antibodies of the Anchoring/Capturing System)

The αCHO antibodies were generated by a standard immunization method of mice like it is described by Dzionek, A. et al, 2000, J. Immunol., 165: 6037-46.

For immunization, one non-stressed 8-week-old female Balb/c mouse was used. On day 0, 4, 7, 10, and 13 the animal was immunized with $5 \times 10^6$ CHO DG44 cells (Invitrogen) in 300 μL sterile 1× Phosphate buffered saline (abbreviated PBS). The injection is applicated into the abdominal cavity. To establish a hybridoma cell line, B-cells from the immunized mouse spleen were fused with the mouse myeloma cell line Sp2/0 Ag14 (AmCell) using polyethylene glycol 1500 (Roche). The fusion was done on day 24.

Titration of αCHO Antibodies (First Antibodies of the Anchoring/Capturing System)

On $10^6$ CHO K1 cells (Invitrogen) per sample, different αCHO purified antibodies were titrated to determine binding. Therefore, pure αCHO antibodies were titrated in different concentrations for 10 min at 4° C. After washing with 1 mL PBS/EDTA/BSA (abbreviated PEB)-buffer, detection was performed by isotype staining with rat αmouse $IgG_{2b}$-R-phycoerythrin (abbreviated PE; PE from Far East Bio-Tec Co) or rat αmouse $IgG_1$-PE (both conjugates from Miltenyi Biotec) at a final dilution of 1/100 for 10 min at 4° C. For flow cytometric analysis MACSQuant® Analyzer (Miltenyi Biotec) was used. The analyses were done using MACSQuantify™ Software (Miltenyi Biotec) and were restricted to viable cells.

The same αCHO antibody clones were also tested on untransfected CHO DG44, CHO Dukx B11 (ATCC) and transfected CHO DG44 cells (pool 3/L cells) and showed positive staining of all three additional CHO cell lines. Transfected CHO DG44 cells (pool 3/L cells) secrete humanized CD303 antibody and had been gene-amplified with 80 nmol/l methotrexate (Sigma).

Coupling of Catch Reagent

Two antibodies are linked covalently by use of functional groups. Thus, catch reagent consisting of an anchor and catch antibody were produced. The used catch reagent was composed of the CHO-specific antibody (clone HA3-21F5.6) and the anti-human IgG antibody clone JH2-4F5.20.1 (both Miltenyi Biotec).

First, catch antibody were activated with succinimidyl-4-(N-maleimidomethyl)cyclohexane-1-carboxylate (abbreviated SMCC; Pierce) for 1 h at 20° C. Afterwards, the reaction was stopped and SMCC was depleted by buffer exchange with a Sephadex column (GE Healthcare). Protein containing fractions were determined with Coomassie (Pierce) staining and pooled. To control activation, coupled maleimide groups were determined with a backward titration using cysteaminium chloride (Merck). The cysteamine reacted with the maleimide groups of the activated antibody and the remaining thiols were detected with Ellman's reagent (Pierce) at $OD_{412}$.

Second, reduction of anchor antibody was performed with 20 mmol/l dithiothreitol (abbreviated DTT; Sigma) for 1 h at 20° C. The excessive DTT was then removed by buffer exchange with a Sephadex column. Protein containing fractions were defined with Coomassie and pooled. The amount of thiols per molecule antibody was determined with Ellman's reagent at $OD_{412}$.

Third, maleimides react with thiol groups at pH 6.5-7.5 to form stable thioether bonds. Coupling was performed for 30 min at 20° C. The reaction was stopped with β-mercaptoethanol (abbreviated β-ME; Merck)) and N-ethylmaleimide (abbreviated NEM; Sigma), incubating each for 15 min at 20° C. The β-ME reacts with free maleimides, whereas the NEM reacts with free thiols. Buffer exchange to PBS/EDTA/Azide-buffer was performed with a PD-10 column (GE Healthcare) and protein-containing fractions were pooled.

Principle of Magnetic Separation with two MS Columns

Cells with distinct characteristics can be separated easily using magnetic activated cell sorting (Miltenyi et al., 1990). For the magnetic labelling of cells, antibody-MicroBead conjugates are used. MicroBeads (abbreviated MB; Miltenyi Biotec) are superparamagnetic particles of approximately 50 nm in diameter. When the MACS® Cell Separation Column (Miltenyi Biotec) is placed into a strong permanent magnet, the MACS Separator (Miltenyi Biotec), a high-gradient magnetic field is induced on the column matrix. This magnetic field within the MACS Cell Separation Column is strong enough to retain cells labeled with minimal amounts of MicroBeads.

For all separations, MS columns (Miltenyi Biotec) were used, which have a capacity of up to $1 \times 10^7$ magnetically labelled cells from up to $2 \times 10^8$ total cells.

Figure 1:
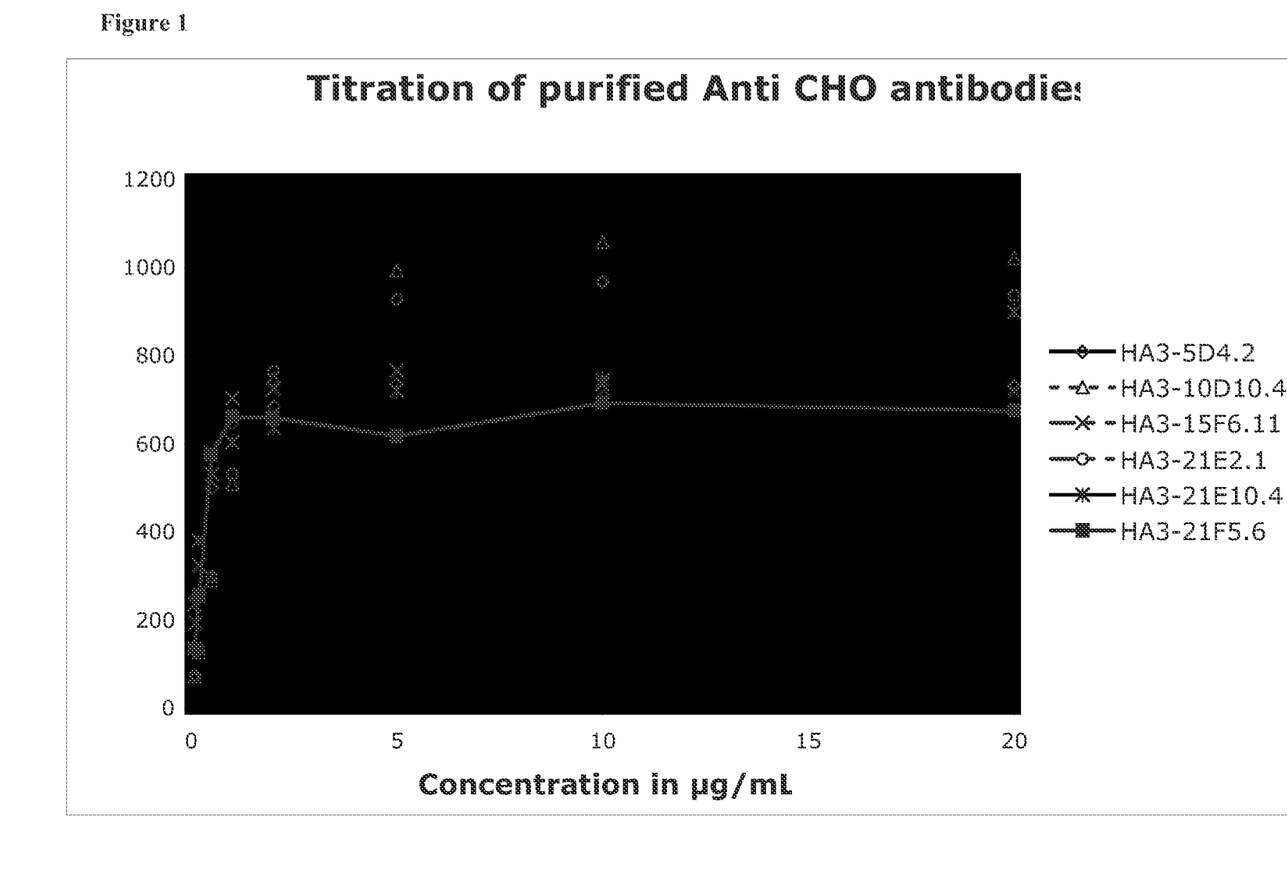
FIG. 1. Titration of first antibodies for anchoring to the extracellular surface of the CHO cell as part of the anchoring/capturing system (αCHO purified antibodies).
Figure 2:
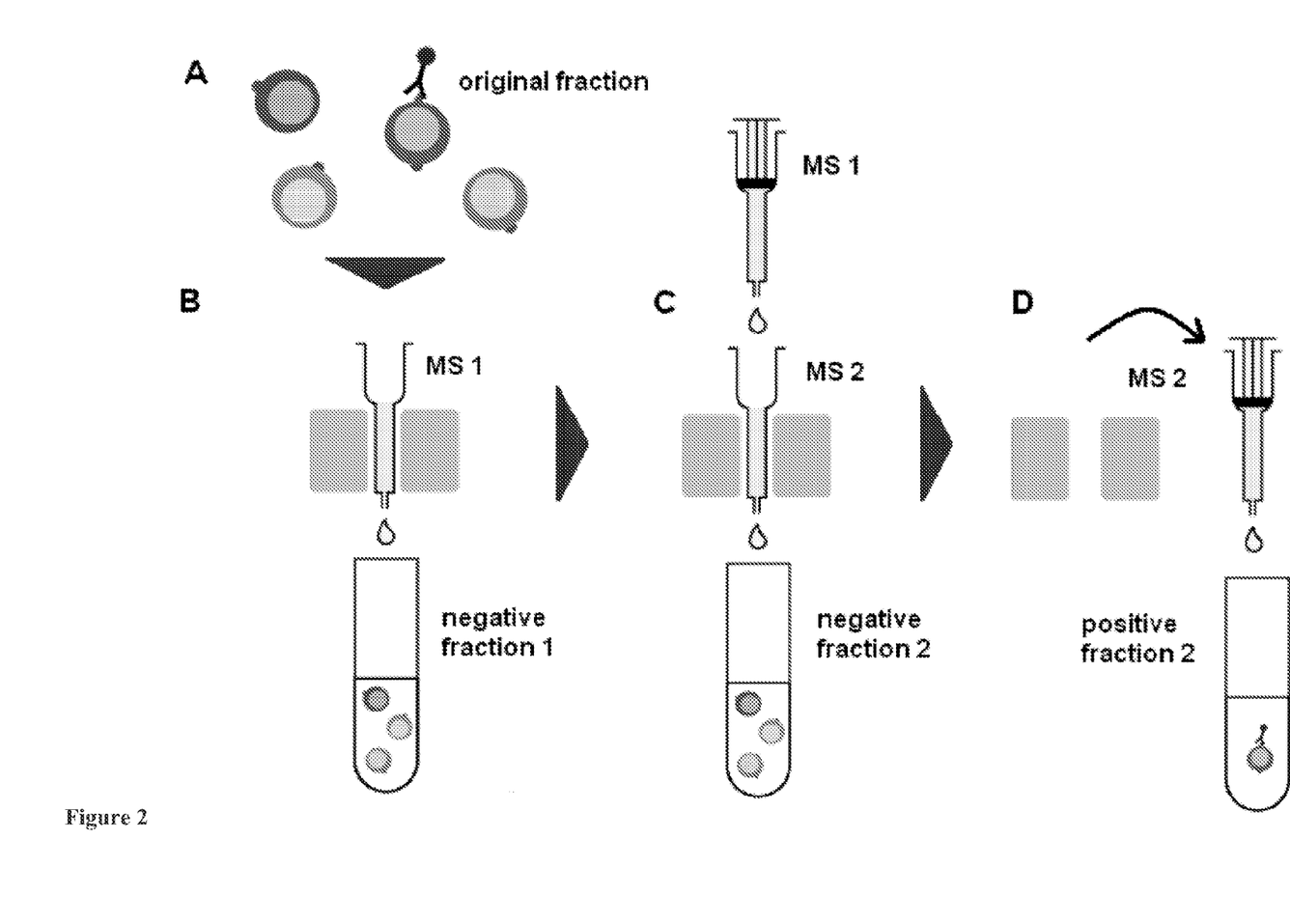
FIG. 2. Strategy of magnetic separation of magnetically labeled CHO cells with two MS columns. Cells were labeled with antibody-MicroBead conjugates (A) and applied onto the first MS column. During the washing steps, unlabelled cells passed through the column into the negative fraction (B). The first MS column was flushed out into the second MS column using 1 mL PBS/EDTA/BSA buffer and the plunger (C). Washing of the second MS column washed out remaining unlabelled cells into the negative fraction 2 (C). Finally, the second MS column was removed from the magnet and flushed out with 0.5 mL buffer, yielding the positive fraction 2.

Before use, columns were equilibrated with 0.5 mL PEB-buffer. The so-called original fraction containing both labeled and unlabelled cells (FIG. 2 A) was applied on the column. The unlabelled cells, which passed through, were collected and the column was washed 3 times with 0.5 mL PEB-buffer. Cells that are labeled with the antibody-MicroBeads conjugates (Miltenyi Biotec) were retained in the column, but unlabelled cells passed through the column and could be collected as the negative fraction (FIG. 2 B). After the column was removed form the magnet, retained cells were eluted with 1 mL buffer as the positively selected cell fraction using the plunger. However, to increase purity, a second MS column was used and cells were directly flushed out of the first column into the second column. Trapped unlabelled cells were then removed by washing with 3×0.5 mL PEB buffer (FIG. 2 C). Finally, the labeled cells were flushed out of the second column with 0.5 mL buffer and collected as the positive fraction 2 (FIG. 2 D).

Human Antibody CHO Capture System

Figure 3:
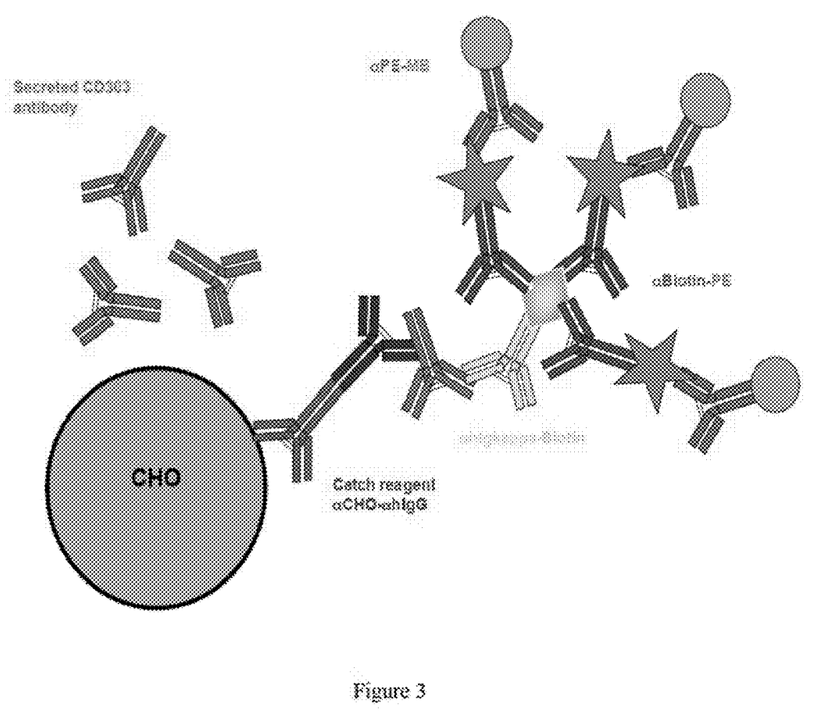
Figure 4:
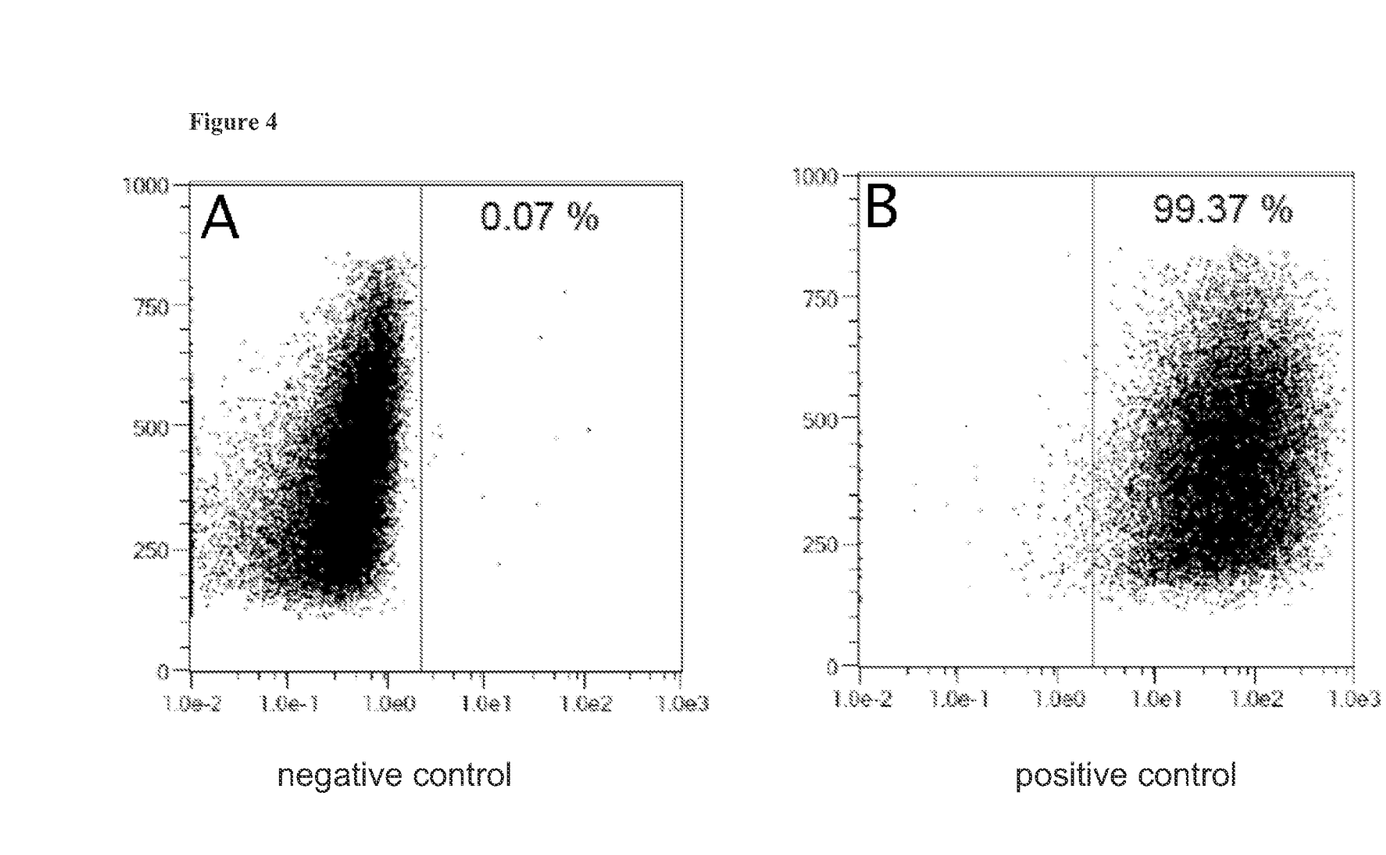

The principle of the present invention (denoted also "Human Antibody CHO Capture System") is schematically shown in FIG. 3.

The CHO pool 3/L cells were singularised with trypsin/EDTA and cell concentration of viable cells was determined with a Neubauer chamber. Small-scale detection approaches with $10^6$ cells as well as large-scale separation approaches with $10^7$ cells were carried out. Staining volume for $10^6$ cells was 100 μL, for $10^7$ cells 1 mL.

The CD303-specific-αCHO/αhuman IgG "catch reagent," (anchoring/capturing system) was diluted in cold CD CHO medium (4° C.) to 7.5 μg/mL and $10^6$ cells were labeled with 100 μL staining solution for 5 min on ice. Afterwards, 10 mL (50 mL for $10^7$ cells) of warm CD CHO medium (37° C.)

were added and cells were allowed to secrete for 1 hr at 37° C. on a MACSmix Tube Rotator (Miltenyi Biotec). To stop secretion, 5 mL of cold PEB-buffer (4° C.) were added and cells were incubated for 5 min on ice. Thereafter, cells were centrifuged (10'/100 g/4° C.) and the supernatant was removed. The αhuman Igκ-biotin detection antibody (clone IS11-1G4.1.4; Miltenyi Biotec) was diluted with cold PEB-buffer (4° C.) to 2 µg/mL and cells were labeled with 100 µL for 10 min on ice. After a washing step with 1 mL cold PEB-buffer (4° C.), cells were stained for 10 min at 4° C. with αbiotin-PE (Miltenyi Biotec) in 110 µL, diluted 1:11 with cold PEB-buffer (4° C.). Afterwards, cells were washed with 1 mL cold PEB-buffer (4° C.), centrifuged (10'/100 g/4° C.) and resuspended in 500 µl PEB. Cells were kept on ice until flow cytometric analysis and propidium iodide (PI) (Sigma) was added prior to measuring.

As a negative control, unstained cells were used, which were resuspended in 500 µL PEB-buffer after singularisation. Other negative controls were cells coated with catch reagent but without detection reagent and cells without catch reagent but stained with detection reagent without a secretion period or after a normal secretion period of 1 hr. Also cells coated with catch reagent and stained for αbiotin-PE were used as negative controls.

Positive controls were stained with catch reagent and with Tysabri-PE (Miltenyi Biotec) for 10 min on ice without a secretion period or with a secretion period of 1 hr. Tysabri (=Natalizumab; Biogen Idec) is a humanized IgG$_4$ antibody for therapeutic use.

After the staining of antibody-secreting cells with αhuman Igκ-biotin and αbiotin-PE, large-scale separation approaches were labelled magnetically using the αPE-MicroBead conjugate. Therefore, αPE-MicroBeads were diluted in cold PEB buffer 1:5 and cells were labeled for 15 min on ice. Afterwards, cells were washed with 10 mL cold PEB-buffer and resuspended in 500 µL PEB.

Before magnetic activated cell sorting, a 10 µL aliquot of the original fraction was preserved for flow cytometric analysis and diluted 1:20 with cold PEB-buffer.

The separation was carried out using 2 MS columns according to the protocol described above. After separation, cells of the original fraction and the second positive fraction were subjected to flow cytometric analysis.

Antibody Production of Cells without and after Enrichment of Cells

CHO pools 3/L cells of the logarithmic growth phase were singularised with trypsin/EDTA and counted with the Neubauer chamber. Then, 2×10$^5$ viable cells were resuspended in a T75 flask containing 20 mL of new CD CHO Medium. After 48 hrs, a 1 mL sample was taken to determine the cell number with the Neubauer chamber. Afterwards, the sample was centrifuged (5'/100 g/20° C.), the supernatant collected and frozen at −20° C.

Elisa

The antibody concentrations of the supernatants were determined by Enzyme Linked ImmunoSorbent Assay (ELISA). For coating, αhuman IgG (Beckman Coulter) was diluted in 0.05 mol/l carbonate buffer, pH 9.6 (Sigma) to 5 µg/mL. In each well, 50 µL were added and incubated for 2 hrs at 37° C. The plate was washed with 3×350 µL 1×KP wash solution (DunnLabortechnik) with 10 sec soaking between washes. For blocking of potential unspecific binding sites, 350 µL PBS/BSA-buffer was added in each well and incubated for 1 h at RT. Then, plates were washed with 3×350 µL KP wash solution. The cell culture supernatant was diluted with PBS/BSA-buffer to fall in the linear portion of the standard curve. For estimated antibody concentrations of 0.02-0.5 µg/mL the sample was diluted 1:20, 1:40, 1:50 and 1:60. If the estimated antibody concentrations were 0.5-5 µg/mL, the sample was diluted 1:200, 1:400, 1:500 and 1:600. Tysabri (Biogen Idec) was used as the standard in the concentrations, 0.781 ng/mL, 1.562 ng/mL, 3.125 ng/mL, 6.25 ng/mL, 12.5 ng/mL and 25 ng/mL. Standards and samples were added in 50 µL duplicates and incubated for 1 hr at 37° C. For two blanks, 50 µL of PBS/BSA were added. After washing with 3×350 µL KP wash solution, αhuman Igκ-Horseradish Peroxidase (abbreviated HRP; Southern Biotech) was added according to manufacturer's instructions. The plate was incubated for 1 hr at 37° C. Then, the plate was washed three times and 50 µL TMB ready to use ELISA substrate (3,3,5,5-tetramethylbenzidine) (abbreviated, TMB; Serva) were added to each well. The reaction was stopped with 10% sulfuric acid and absorbance was measured at 450 nm with the ELISA reader (MWG Biotec).

For the calculation of the antibody concentration, a standard curve was created.

Intracellular Staining of Cells

To allow antibody binding to intracellular proteins, cells need to be fixed with Inside Fix (3.7% Formaldehyde solution; Miltenyi Biotec) and permeabilised with Inside Perm (0.5% Saponin solution; Miltenyi Biotec).

First, 10$^6$ cells (Pool 3/L cells not enriched or enriched by Human Antibody CHO Capture System and afterwards cultivated for 16 days) were resuspended in 100 µL of PBS-buffer and mixed with 100 µL of Inside Fix. Cells were then incubated for 30 min at 20° C. Next, 1 mL PEB-buffer was added and cells were pelleted (5'/200 g/20° C.). Fixed cells can be resuspended in 100 µL PBS/EDTA-buffer and stored at 4° C. for one week.

For staining, cells were washed with 1 mL Inside Perm buffer and pelleted (5'/200 g/20° C.). Afterwards, cells were pre-incubated with 100 µL Inside Perm for 20 min at 20° C. Following fluorescent antibodies were used: αhuman Igκ-PE, αhuman Igκ-allophycocyanin (APC) and α human IgG$_4$-FITC (positive staining) and αhuman Igκ-PE or APC and α human IgG$_{2b}$-FITC (negative staining) All conjugates were from Miltenyi Biotec. Fluorochromes are added and incubated for 20 min at 20° C. Cells were washed with 1 mL Inside Perm and resuspended in 500 µL PEB-buffer. Analysis was performed by flow cytometry.

As described, CHO pool 3/L cells containing a mixture of antibody secreting and non-secreting cells were subjected to separation by the Human Antibody CHO Capture System. Unseparated as well as enriched cells were further cultivated for 16 days and then analyzed for antibody production (Table 1). As expected, the accumulated antibody was higher in enriched cells.

TABLE 1

Antibody production of CHO cells without and after enrichment of cells in secretion assay according to a preferred embodiment of the invention tested by ELISA and intracellular staining

| procedure | accumulated antibody in well [ng/mL] | producer rate [%] |
| --- | --- | --- |
| w/o separation | 64.15 | 2.69 |
| after separation | 317.75 | 53.11 |

All references cited herein are herein incorporated by reference in entirety.

We claim:

1. A Chinese hamster ovary (CHO) cell bound to an anchoring/capturing system for selecting or analyzing a CHO cell according to a product secreted by said CHO cell, comprising a first antibody or a first antigen-binding fragment that binds an extracellular surface target of said CHO cell and a second antibody or a second antigen-binding fragment that binds the secreted CHO cell product, wherein the first antibody or first antigen-binding fragment is covalently linked to the second antibody or second antigen-binding fragment.

2. A method for selecting or analyzing a Chinese hamster ovary (CHO) cell according to a product secreted by the CHO cell, comprising:
   (a) binding an anchoring/capturing system to the surface of the CHO cell for capturing the secreted CHO cell product, wherein the anchoring/capturing system comprises
       a first antibody or a first antigen-binding fragment that binds an extracellular surface target of the CHO cell, and
       a second antibody or a second antigen-binding fragment for binding the secreted product, wherein the first antibody or first antigen-binding fragment is covalently linked to the second antibody or second antigen-binding fragment;
   (b) culturing the cell under conditions wherein the product is secreted and is specifically bound to the second antibody or to the second antigen-binding fragment;
   (c) labeling the secreted product with a detectable label; and
   (d) selecting or analyzing the CHO cell on the basis of the bound and labeled secreted CHO cell product.

3. The method of claim 2, wherein the cells having product bound to the second antibody or the second antigen-binding, fragment are not lysed as part of the selection or analysis.

4. The method of claim 2, wherein the secreted product is a protein.

5. The method of claim 4, wherein said protein comprises an antibody or witigen-binding fragment thereof.

6. The method of claim 2, wherein the secreted product is an antibody selected from the group consisting of humanized antibodies, chimeric antibodies, human antibodies and antigen-binding fragments thereof.

7. The method of claim 2, wherein the detectable label comprises at least one of magnetic particles, fluorophores, radioactive isotopes, haptens or chromophores.

8. The method of claim 2, wherein the secreted product is a CD303 (BDCA-2) antibody or a fragment thereof.

9. A method for selecting or analyzing a Chinese hamster ovary (CHO) cell according to a CD303 (BDCA-2) antibody or a CD303-binding fragment thereof secreted by said CHO cell, comprising:
   (a) binding an anchoring/capturing system to the surface of said CHO cell for capturing the secreted CD303 (BDCA-2) antibody or fragment thereof, wherein the anchoring/capturing system comprises
       a first antibody or a first antigen-binding fragment that binds an extracelltaar surface target of said CHO cell, and
       a second antibody or a second antigen-binding fragment for binding the secreted CD303 (BDCA-2) antibody or fragment thereof, wherein the first antibody or first antigen-binding fragment is covalently linked to the second antibody or second antigen-binding fragment;
   (b) culturing the cell under conditions wherein the CD303 (BDCA-2) antibody or fragment thereof is secreted and is specifically bound to the second antibody or to the second antigen-binding fragment;
   (c) labeling the secreted CD303 (BDCA-2) antibody or fragment thereof with a detectable label; and
   (d) selecting or analyzing the CHO cell on the basis of the bound and labeled secreted CD303 (BDCA-2) antibody or fragment thereof product.

* * * * *